(12) United States Patent
Brookshire et al.

(10) Patent No.: US 10,449,347 B2
(45) Date of Patent: Oct. 22, 2019

(54) TATTOO MACHINE TUBE WITH INK RESERVOIR

(71) Applicants: Mykol Travis Brookshire, Ada, OK (US); Garrett Gage Brookshire, Ada, OK (US)

(72) Inventors: Mykol Travis Brookshire, Ada, OK (US); Garrett Gage Brookshire, Ada, OK (US)

( * ) Notice: Subject to any disclaimer, the term of this patent is extended or adjusted under 35 U.S.C. 154(b) by 0 days.

(21) Appl. No.: 14/847,733

(22) Filed: Sep. 8, 2015

(65) Prior Publication Data

US 2016/0184573 A1  Jun. 30, 2016

Related U.S. Application Data

(60) Provisional application No. 62/047,071, filed on Sep. 8, 2014.

(51) Int. Cl.
*A61M 37/00* (2006.01)

(52) U.S. Cl.
CPC .............................. *A61M 37/0084* (2013.01)

(58) Field of Classification Search
CPC .......... A61M 37/0084; A61M 37/0076; A61M 37/0092
See application file for complete search history.

(56) References Cited

U.S. PATENT DOCUMENTS

| | | | | |
|---|---|---|---|---|
| 3,039,467 | A | * | 6/1962 | Stone .................... A01K 11/005 30/367 |
| 4,435,099 | A | * | 3/1984 | Murahara ................ B43K 5/18 346/140.1 |
| 4,671,277 | A | * | 6/1987 | Beuchat ............ A61M 37/0076 606/185 |
| 5,054,339 | A | | 10/1991 | Yacowitz |
| 6,345,553 | B1 | * | 2/2002 | Adler ................ A61M 37/0076 30/362 |
| 6,505,530 | B2 | | 1/2003 | Adler et al. |
| 2004/0153113 | A1 | * | 8/2004 | Matera, Jr. ........... A01K 11/005 606/186 |
| 2010/0154597 | A1 | * | 6/2010 | South ................ A61M 37/0084 81/9.22 |
| 2013/0226211 | A1 | | 8/2013 | Xiao |

* cited by examiner

*Primary Examiner* — Julie A Szpira
(74) *Attorney, Agent, or Firm* — Dunlap Codding, PC.

(57) ABSTRACT

A tube for a tattoo machine has a tube portion and a grip portion. The tube portion has a first ink storage cavity, and the grip portion extends about the tube portion so that the proximal end, the distal end, and the sidewall of the grip portion cooperate with the tube portion to define a second ink storage cavity. The second ink storage cavity is in fluid communication with a needle receiving passage of the tube portion and at least a portion of the sidewall is flexible so that upon application of a compressive force on the flexible portion of the grip portion, a volume of ink is transferable from the second ink storage cavity, into the needle receiving passage, and into the first ink storage cavity.

11 Claims, 1 Drawing Sheet

TATTOO MACHINE TUBE WITH INK RESERVOIR

CROSS-REFERENCE TO RELATED APPLICATIONS

This application claims priority to U.S. Provisional Application Ser. No. 62/047,071, filed on Sep. 8, 2014, the entirety of which being hereby expressly incorporated herein by reference.

BACKGROUND

Tattooing involves the placement of ink or pigment into the skin's dermis. The most common method of tattooing today is the electric tattoo machine, which places ink into the skin via a single needle or a group of needles that are connected to an oscillating unit. The unit rapidly and repeatedly drives the needles in and out of the skin, usually 80 to 150 times a second. A hollow cylinder or tube is attached to the tattoo machine to guide the needles and to hold a volume of ink. A portion of the tube often has a larger external diameter than the rest of the tube. This enlarged portion of the tube functions as hand grip for the tattoo artist. As the needles move in an out of the skin, the ink from the tube is carried by gravity from the tube, down the needles, and into the skin.

During the tattooing process, the tip of the tube is required to be dipped in a container of ink once the ink held in the tip is depleted. To obtain dark, permanent tattoos, it is important to use adequate amounts of ink on the tips of the tattoo needle. In the process of dipping the needle into the ink, if the needle is not dipped sufficiently frequently, a pale, poorly visible tattoo may result. However, frequent dipping is time consuming and increases the chances the needle will strike a hard surface and be damaged when dipped into the ink supply. In addition to the economic loss when the needle is damaged and the increased time to create a tattoo, the damaged needle, if used, will cause pain while tattooing. The damaged tips may also damage the skin in a way that affects the quality of the tattoo, as well as result in swelling and bleeding at the tattoo site.

To overcome the problems associated with frequent dipping, some tattooing apparatus are known which employ a reservoir of ink or pigment to supply the needle with pigment without requiring dipping. However, such apparatus have not been accepted by tattoo artist for a variety of reasons. For example, some apparatus extend the reservoir of the tube in a way that affects the look and feel of the tattooing machine making it undesirable to use. Other apparatus provide an inadequate ink supply.

To this end, a need exists for an improved tube for a tattoo machine with an ink reservoir that is easy to use. It is to such a tube that the inventive concepts disclosed herein and claimed are directed.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale, or in schematic in the interest of clarity and conciseness. Not every component may be labeled in every drawing. Like reference numerals in the figures may represent and refer to the same or similar element or function. In the drawings.

DETAILED DESCRIPTION OF EXEMPLARY EMBODIMENTS

Figure 1:
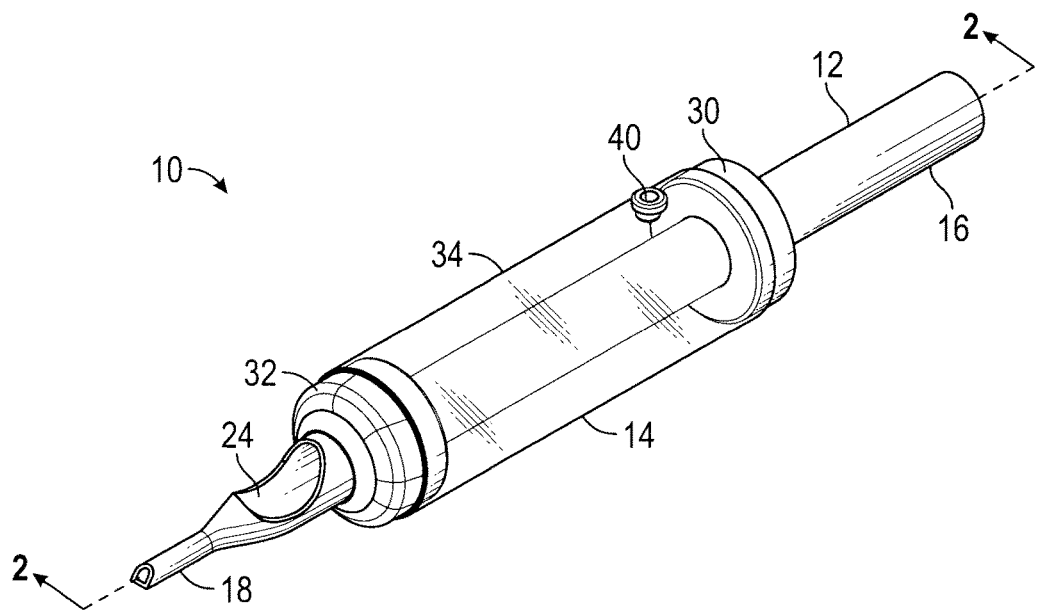
FIG. 1 is a perspective view of a tube constructed in accordance with the inventive concepts disclosed herein.

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts disclosed and claimed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements or steps is not necessarily limited to only those elements or steps and may include other elements, steps, or features not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Throughout this disclosure and the claims, the terms "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, or combinations thereof, for example.

The use of the term "at least one" will be understood to include one as well as any quantity more than one, including but not limited to each of, 2, 3, 4, 5, 10, 15, 20, 30, 40, 50, 100, and all integers therebetween. The term "at least one" may extend up to 100 or 1000 or more, depending on the term to which it is attached; in addition, the quantities of 100/1000 are not to be considered limiting, as higher limits may also produce satisfactory results. Singular terms shall include pluralities and plural terms shall include the singular unless indicated otherwise.

The term "or combinations thereof" as used herein refers to all permutations and/or combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment, although the inventive concepts disclosed herein are intended to encompass all combinations and permutations including one or more of the features of the embodiments described herein.

Referring now to the drawings, a tube 10 constructed in accordance with the inventive concepts disclosed herein is illustrated. The tube 10 is designed to be used with conventional tattoo machines (not shown) that support one end of the tube 10 and causes a needle or grouping of needles to reciprocate within the tube 10. Examples of tattoo machines are disclosed in U.S. Publication No. 2009/0090218, which is hereby expressly incorporated herein by reference.

Figure 2:
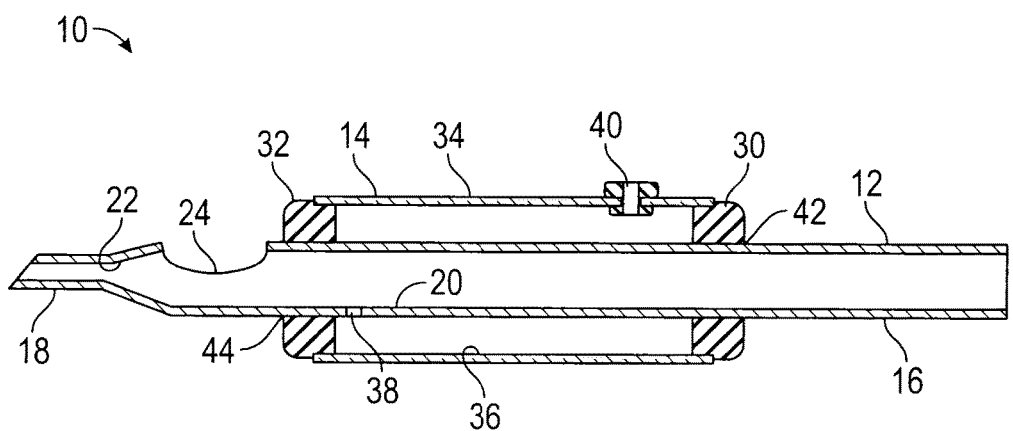
FIG. 2 is a cross sectional view taken along line 2-2 of FIG. 1.

The tube 10 includes a tube portion 12 and a grip portion 14. The tube portion 12 has a diameter, a proximal end 16, a distal end 18, and a needle receiving passage 20 (FIG. 2) extending through the tube portion 12 from the proximal end 16 to the distal end 18. The proximal end 16 is adapted to be connected to the tattoo machine (not shown) with a needle (also not shown) connected to the tattoo machine. The needle extends through the needle receiving passage 20 with a tip of the needle extending beyond the distal end 18 of the tube portion 12. The needle receiving passage 20 at the distal end 18 of the tube portion 12 defines an ink storage cavity 22. The tube portion 12 further has an opening 24 formed near the distal end 18 to facilitate cleaning of the ink storage cavity 22. The tube portion 12 may be made from a suitable plastic that may be sterilized and packaged in FDA approved packaging for single use purposes.

The grip portion 14 has a proximal end 30, a distal end 32, and a sidewall 34 extending between the proximal end 30 and the distal end 34, and a diameter greater than the diameter of the tube portion 12. The grip portion 14 extends about the tube portion 12 so that the proximal end 30, the distal end 32, and the sidewall 34 of the grip portion 14 cooperate with the tube portion 12 to define a second ink storage cavity 36. The second ink storage cavity 36 is in fluid communication with the needle receiving passage 20 of the tube portion 12 so that ink may be selectively transferred from the second ink storage cavity 36 to the first ink storage cavity 22 without requiring the distal end 18 of the tube portion 12 to be dipped in an ink container.

In one embodiment, the tube portion 12 is provided with a discharge passage 38 interposed between the needle receiving passage 20 and the second ink storage cavity 36. The discharge passage 38 may be sized to prevent the passage of ink from the second ink storage cavity 36 without the application of force. In one version, the discharge passage 38 may have a diameter of about ½2 of an inch. The discharge passage 38 may be positioned adjacent the distal end 32 of the grip portion 13 on an opposing side of the opening 24 of the tube portion 12.

To apply a dispensing force to ink contained in the second ink storage cavity 36, all or a portion of the sidewall 34 of the grip portion 14 may be sufficiently flexible so that upon squeezing or application of a compressive force to sidewall 34, ink is caused to pass from the second ink storage cavity 36 through passage 38 and into the needle receiving passage 20 wherein gravity will carrying the ink into the first ink storage cavity 22. The sidewall 34 may be constructed of a suitable flexible tubular plastic.

The sidewall 34 may include an inlet passage 40 that permits ink to be inserted into the second ink storage cavity 36. In one embodiment, the discharge passage 38 and the inlet passage 40 are positioned on opposing sides of the tube portion 12.

The grip portion 14 may be formed to be detachable from the tube portion 12. The proximal end 30 and the distal end 32 of the grip portion 14 may be provided with holes 40 and 42, respectively, for slideably receiving the tube portion 12 and be formed of a rubber or some other suitable material capable of forming a liquid seal about the tube portion 12. The grip portion 14 may extend concentrically about the tube portion 12 such that the second ink storage cavity 36 completely encircles the tube portion 12. The grip portion 14 is illustrated as being substantially cylindrically shaped, but it will be appreciated that the grip portion 14 may be formed in a variety of shapes and sizes.

In use, the tube 10 is attached to a tattoo machine and ink is inserted into the second ink storage cavity 36 via the inlet passage 40. By the application of a compressive force to the sidewall 34 of the grip portion 14, ink is caused to pass from the second ink storage cavity 36 through the discharge passage 38 and into the needle receiving passage 20 wherein gravity will carry the ink into the first ink storage cavity 22. Prior to depletion of the ink in the first ink storage cavity 22, the user may again apply a compressive force to the sidewall 34 of the grip portion 14 and cause ink to pass from the second ink storage cavity 36 through passage 38 and into the needle receiving passage 20 wherein gravity will carrying the ink into the first ink storage cavity 22 without requiring the user to dip the distal end 18 of the tube portion 12 in a container of ink.

From the above description, it is clear that the inventive concepts disclosed herein are well adapted to carry out the objects and to attain the advantages mentioned herein as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concept disclosed and claimed herein.

What is claimed is:

1. A tube for a tattoo machine, comprising:
a tube portion having a diameter, a proximal end, a distal end, and a needle receiving passage extending through the tube from the proximal end to the distal end, the proximal end being connectable to a tattoo machine with a needle of the tattoo machine extending through the needle receiving passage, the needle receiving passage at the distal end of the tube portion defining a first ink storage cavity; and a grip portion having a proximal end, a distal end, a sidewall extending between the proximal end and the distal end, and a diameter greater than the diameter of the tube portion, the grip portion extending about the tube portion so that the proximal end, the distal end, and the sidewall of the grip portion cooperate with the tube portion to define a second ink storage cavity, the second ink storage cavity surrounding the tube portion in a concentric arrangement and being in fluid communication with the needle receiving passage of the tube portion, at least a portion of the sidewall being flexible so that upon application of a compressive force on the flexible portion of the grip portion, a volume of ink is transferrable from the second ink storage cavity, into the needle receiving passage, and into the first ink storage cavity.

2. The tube of claim 1, wherein the grip portion extends concentrically about the tube portion.

3. The tube of claim 2, wherein the grip portion is substantially cylindrically shaped.

4. A tube for a tattoo machine having a needle, comprising:
   a tube portion having a diameter, a proximal end, a distal end, and a needle receiving passage extending through the tube from the proximal end to the distal end, the proximal end being connectable to a tattoo machine with a needle of the tattoo machine extending through the needle receiving passage, the needle receiving passage at the distal end of the tube portion defining a first ink storage cavity; and
   a grip portion having a proximal end, a distal end, a sidewall extending between the proximal end and the distal end, and a diameter greater than the diameter of the tube portion, the grip portion extending about the tube portion so that the proximal end, the distal end, and the sidewall of the grip portion cooperate with the tube portion to define a second ink storage cavity, the second ink storage cavity surrounding the tube portion in a concentric arrangement and being in fluid communication with the needle receiving passage of the tube portion via a discharge passage formed in the tube portion surrounded by the second ink storage cavity and interposed between the needle receiving passage and the second ink storage cavity so that ink in the second ink storage cavity passes directly into the needle receiving passage from the second ink storage cavity, at least a portion of the sidewall being flexible so that upon application of a compressive force on the flexible portion of the grip portion, a volume of ink is transferrable from the second ink storage cavity, into the needle receiving passage, and into the first ink storage cavity.

5. The tube of claim 4, wherein the sidewall has a passage defining an inlet passage for filling the second ink storage cavity with ink, and wherein the discharge passage and the inlet passage are positioned on opposing sides of the tube portion.

6. The tube of claim 5, wherein the discharge passage is positioned adjacent the distal end of the grip portion.

7. The tube of claim 6, wherein the grip portion extends concentrically about the tube portion.

8. The tube of claim 7, wherein the grip portion is substantially cylindrically shaped.

9. A tube in combination with a tattoo machine with a needle, the tube comprising:
   a tube portion having a diameter, a proximal end, a distal end, and a needle receiving passage extending through the tube from the proximal end to the distal end, the proximal end connected to the tattoo machine with the needle of the tattoo machine extending through the needle receiving passage, the needle receiving passage at the distal end of the tube portion defining a first ink storage cavity; and
   a grip portion having a proximal end, a distal end, a sidewall extending between the proximal end and the distal end, and a diameter greater than the diameter of the tube portion, the grip portion extending about the tube portion so that the proximal end, the distal end, and the sidewall of the grip portion cooperate with the tube portion to define a second ink storage cavity, the second ink storage cavity surrounding the tube portion in a concentric arrangement and being in fluid communication with the needle receiving passage of the tube portion, at least a portion of the sidewall being flexible so that upon application of a compressive force on the flexible portion of the grip portion, a volume of ink is transferrable from the second ink storage cavity, into the needle receiving passage, and into the first ink storage cavity.

10. The combination of claim 9, wherein the grip portion extends concentrically about the tube portion.

11. The combination of claim 10, wherein the grip portion is substantially cylindrically shaped.

* * * * *